United States Patent
Greenberg et al.

(10) Patent No.: US 9,597,495 B2
(45) Date of Patent: *Mar. 21, 2017

(54) LOCATING A NEURAL PROSTHESIS USING IMPEDANCE AND ELECTRODE HEIGHT

(75) Inventors: Robert J. Greenberg, Los Angeles, CA (US); Jone Fine, Seattle, WA (US); Arup Roy, Valencia, CA (US); Matthew J. McMahon, Los Angeles, CA (US); Mark S. Humayun, Glendale, CA (US); James David Welland, Valencia, CA (US); Alan M. Horsager, Los Angeles, CA (US); Dao Min Zhou, Saugus, CA (US); Amy Hines, Monterey Park, CA (US); Sumit Yadav, Los Angeles, CA (US); Rongqing Dai, Valencia, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/452,300

(22) Filed: Apr. 20, 2012

(65) Prior Publication Data

US 2012/0203293 A1  Aug. 9, 2012

Related U.S. Application Data

(62) Division of application No. 11/607,201, filed on Dec. 1, 2006, now Pat. No. 8,180,454.

(60) Provisional application No. 60/741,810, filed on Dec. 1, 2005, provisional application No. 60/853,477, filed on Oct. 20, 2006.

(51) Int. Cl.
  *A61N 1/05* (2006.01)
  *A61N 1/36* (2006.01)
  *A61N 1/372* (2006.01)

(52) U.S. Cl.
  CPC ....... *A61N 1/0543* (2013.01); *A61N 1/36046* (2013.01); *A61N 1/37247* (2013.01)

(58) Field of Classification Search
  CPC .......................... A61N 1/0543; A61N 1/36046
  USPC ........................................................ 607/54
  See application file for complete search history.

(56) References Cited

U.S. PATENT DOCUMENTS

| | | |
|---|---|---|
| 4,573,481 A | 3/1986 | Bullara |
| 4,577,642 A | 3/1986 | Stokes |
| 4,628,933 A | 12/1986 | Michelson |

(Continued)

OTHER PUBLICATIONS

Humayun et al. Visual Perception in a Blind Subject with a Chronic Microelectronic Retinal Prosthesis. Vision Research. 2003; 43:24:2573-2581.*

(Continued)

*Primary Examiner* — Christopher D Koharski
*Assistant Examiner* — Jeremiah Kimball
(74) *Attorney, Agent, or Firm* — Scott Dunbar; Tomas Lendvai

(57) ABSTRACT

The invention is a method of identifying a preferred location for an electrode array to the neural characteristics of an individual subject. The response to electrical neural stimulation varies from subject to subject and array location to array location. Measure of impedance may be used to predict the electrode height from the neural tissue and, thereby, predict the preferred location. Alternatively, electrode height may be measured directly to predict the preferred location.

7 Claims, 17 Drawing Sheets

(56) References Cited

U.S. PATENT DOCUMENTS

| | | | |
|---|---|---|---|
| 4,837,049 A | 6/1989 | Byers et al. | |
| 5,109,844 A | 5/1992 | de Juan, Jr. et al. | |
| 5,215,088 A | 6/1993 | Normann et al. | |
| 5,341,807 A * | 8/1994 | Nardella | 600/381 |
| 5,935,155 A * | 8/1999 | Humayun et al. | 607/54 |
| 6,157,861 A | 12/2000 | Faltys et al. | |
| 6,205,360 B1 | 3/2001 | Carter et al. | |
| 6,208,894 B1 | 3/2001 | Schulman | |
| 6,400,989 B1 | 6/2002 | Eckmiller | |
| 6,415,185 B1 | 7/2002 | Maltan | |
| 6,445,951 B1 * | 9/2002 | Mouchawar | A61N 1/3931 607/28 |
| 6,458,157 B1 | 10/2002 | Suaning | |
| 6,522,928 B2 | 2/2003 | Whitehurst et al. | |
| 6,920,358 B2 | 7/2005 | Greenberg et al. | |
| 7,317,948 B1 * | 1/2008 | King | A61N 1/3615 600/547 |
| 7,819,869 B2 * | 10/2010 | Godara et al. | 606/41 |
| 2003/0199938 A1 * | 10/2003 | Smits et al. | 607/27 |
| 2004/0172098 A1 | 9/2004 | Greenberg et al. | |
| 2005/0085869 A1 * | 4/2005 | Tehrani et al. | 607/42 |
| 2006/0135999 A1 * | 6/2006 | Bodner et al. | 607/4 |

OTHER PUBLICATIONS

Siemionow et al. Measurement of tissue electrical impedance confirms stereotactically localized internal segment of the globus pallidus during surgery. Neurosci Methods. Mar. 15, 2000;96(2):113-7.*

Mahadevappa et al. Perceptual Thresholds and Electrode Impedance in Three Retinal Prosthesis Subjects. IEEE Trans Neural Syst Rehabil Eng. Jun. 2005;13(2):201-6.*

Eugene De Juan, Retinal Tacks, American Journal of Ophthalmology 99: pp. 272-274, Mar. 1985.

* cited by examiner

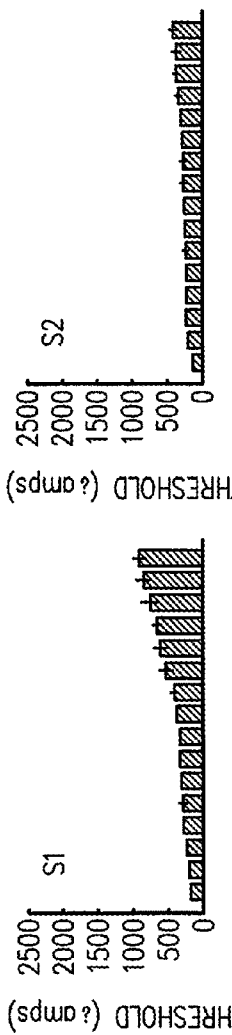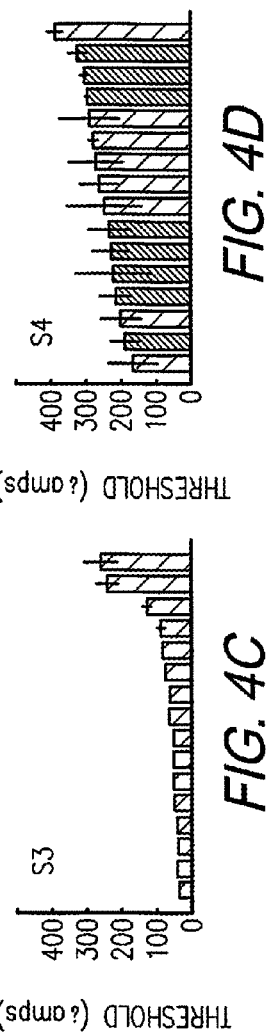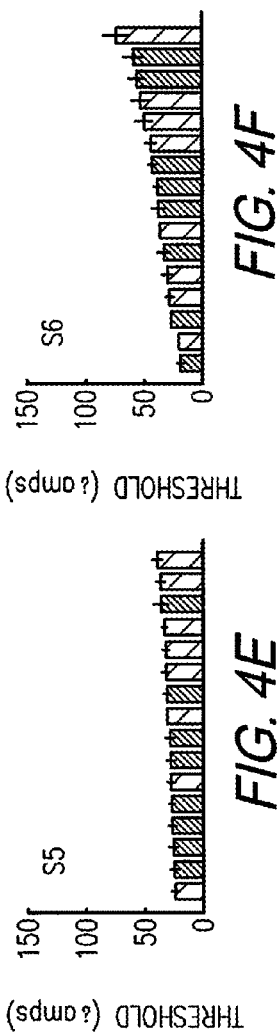
FIG. 4A, FIG. 4B, FIG. 4C, FIG. 4D, FIG. 4E, FIG. 4F

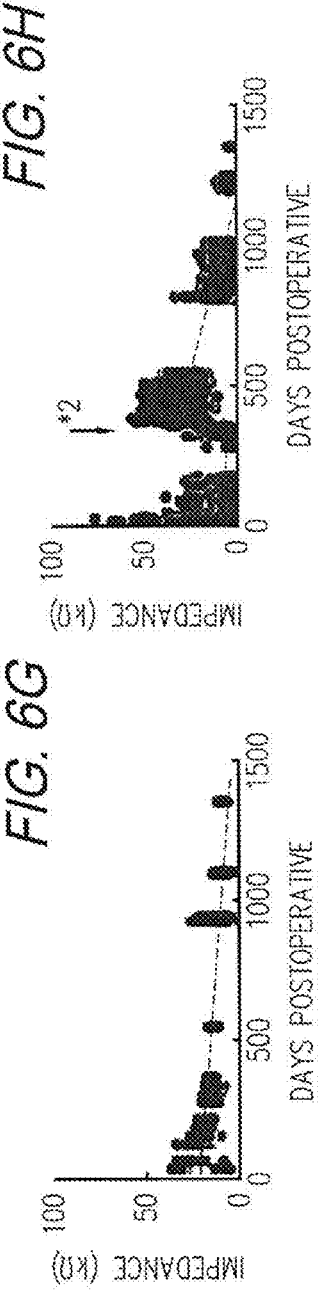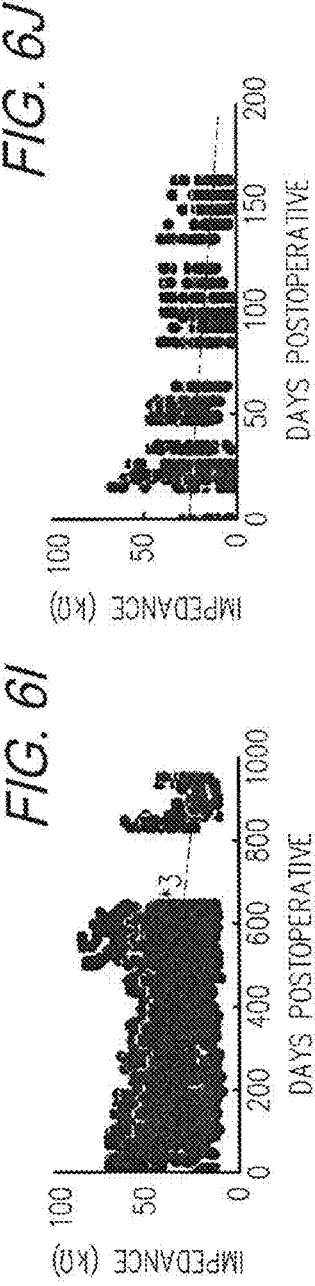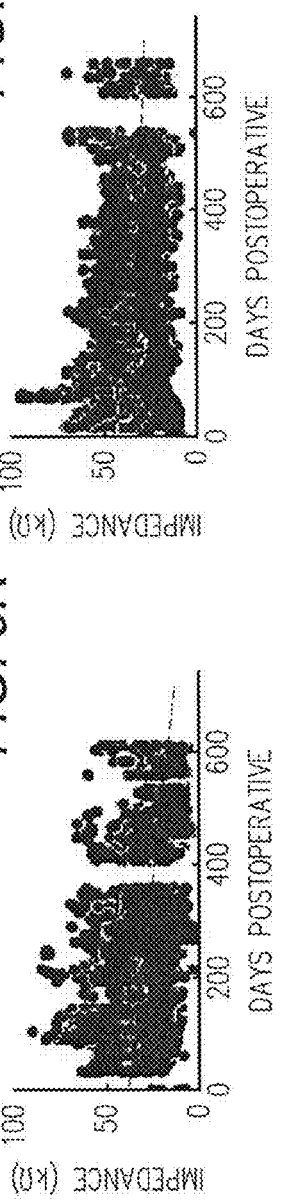

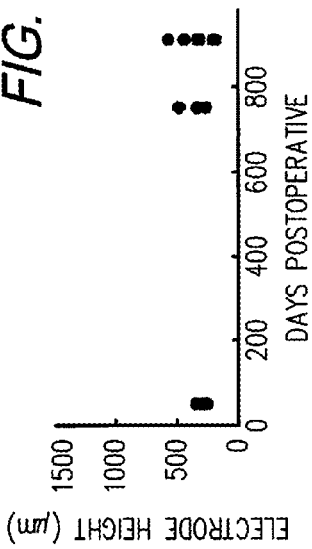
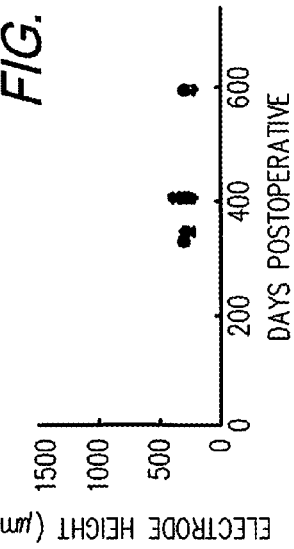
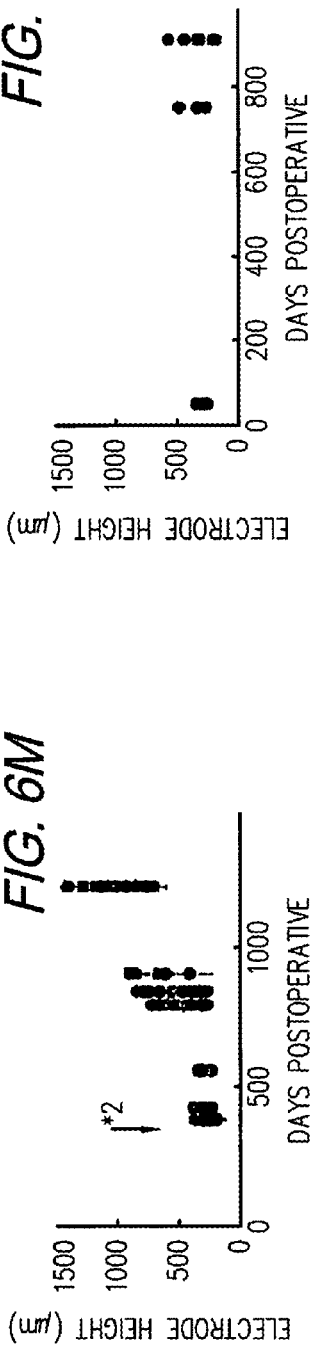
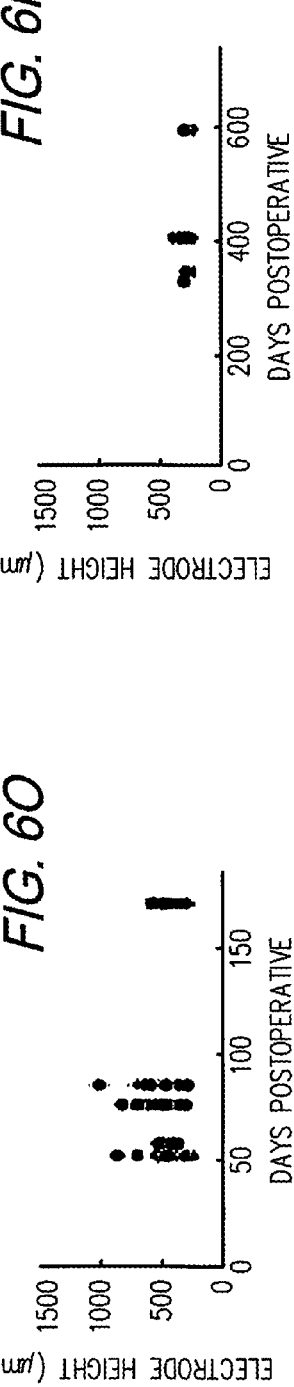
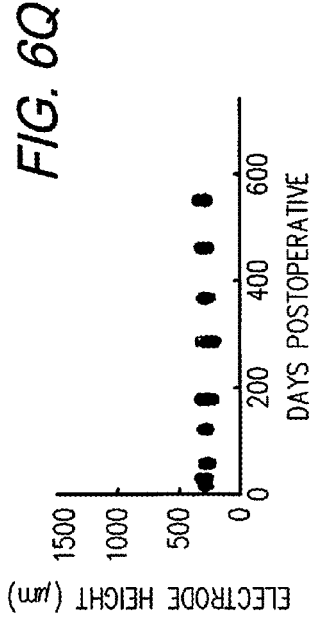

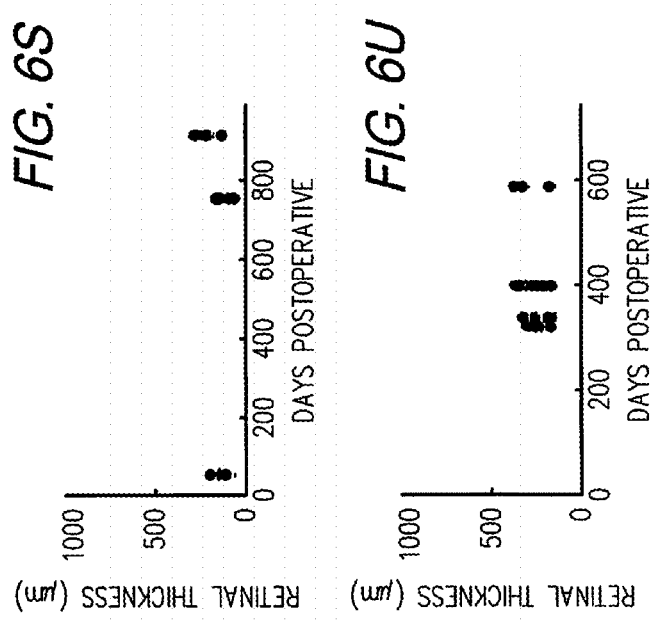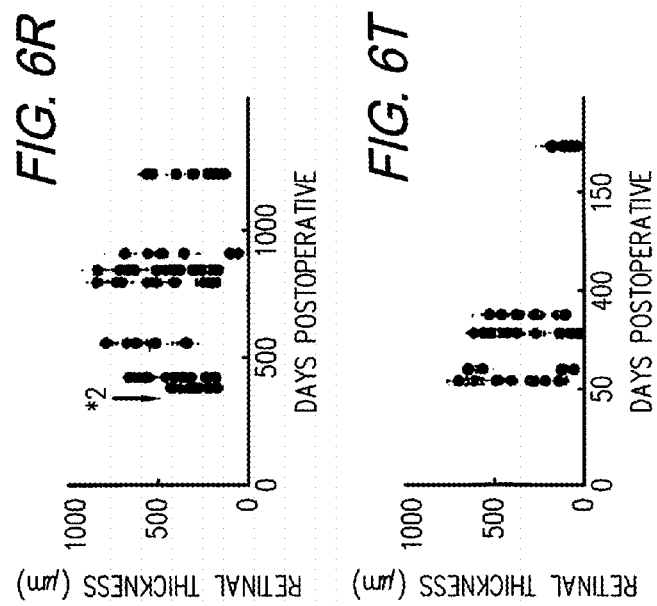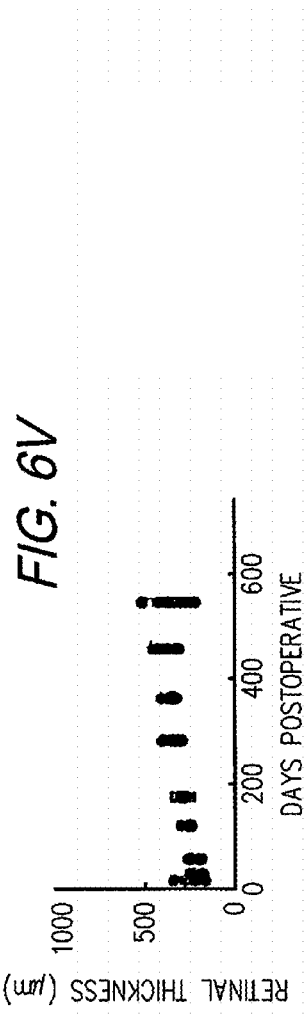

LOCATING A NEURAL PROSTHESIS USING IMPEDANCE AND ELECTRODE HEIGHT

CROSS REFERENCE TO RELATED APPLICATIONS

This application is a divisional application of, and claims priority to, U.S. application Ser. No. 11/607,201, filed Dec. 1, 2006, for Fitting a Neural Prosthesis Using Impedance and Electrode Height, now U.S. Pat. No. 8,180,454, which claims priority to U.S. Provisional Patent Applications 60/741,810, filed Dec. 1, 2005, for Correlation of Electrode Height, Stimulation Threshold and Impedance in a Retinal Prosthetic Implant, and 60/853,477, filed Oct. 20, 2006, for Real Time Electrode Impedance Measurement and Data Display for an Implantable Device. This application is related to and incorporates herein by reference, U.S. patent application Ser. Nos. 10/864,590, filed Jun. 8, 2004, for Automatic Fitting for a Visual Prosthesis, now U.S. Pat. Nos. 7,483,751, and 11/357,680, filed Feb. 16, 2006, for Fitting of Brightness in a Visual Prosthesis, now U.S. Pat. No. 7,738,962.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of optimizing neural stimulation levels for artificial vision.

BACKGROUND OF THE INVENTION

In 1755 LeRoy passed the electrical discharge of a Leyden jar through the eye orbit of a man who was blind from cataracts and the subject saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of subjects. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the subject perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

In addition to the electrode arrays described above, there are several methods of mapping a high resolution camera image to a lower resolution electrode array. U.S. Pat. No. 6,400,989 to Eckmiller describes spatio-temporal filters for controlling patterns of stimulation in an array of electrodes. The assignee of the present applications has three related U.S. patent application Ser. Nos. 09/515,373, filed Feb. 29, 2000, entitled Retinal Color Prosthesis for Color Sight Restoration; 09/851,268, filed May 7, 2001, entitled Method, Apparatus and System for Improved Electronic Acuity and Perceived Resolution Using Eye Jitter Like Motion; filed on current date herewith, entitled User Directed Pixel Re-Mapping. All three applications are incorporated herein by reference.

Each person's response to neural stimulation differs. In the case of retinal stimulation, a person's response varies from one region of the retina to another. In general, the retina is more sensitive closer to the fovea. Responses are also very sensitive to the distance of the electrode array from the retinal surface. Any stimulation with magnitude less than the threshold of perception is ineffective in producing an image. Stimulation beyond a maximum level will be painful and possibly dangerous to the subject. It is therefore, important to map any video image to a range of stimulation values between the minimum and maximum for each individual electrode. With a simple retinal prosthesis, it is possible to adjust the stimulation manually by stimulating and questioning the subject. As resolution (number of electrodes) increases, it is tedious or impossible to adjust each electrode by stimulating and eliciting a subject response.

A manual method of fitting or adjusting the stimulation levels of an auditory prosthesis is described in U.S. Pat. No. 4,577,642, Hochmair et al. Hochmair adjusts the auditory prosthesis by having a user compare a received signal with a visual representation of that signal.

A more automated system of adjusting an auditory prosthesis using middle ear reflex and evoked potentials is described in U.S. Pat. No. 6,157,861, Faltys et al. An alternate method of adjusting an auditory prosthesis using the stapedius muscle is described in U.S. Pat. No. 6,205,360, Carter et al. A third alternative using myogenic evoked response is disclosed in U.S. Pat. No. 6,415,185, Maltan.

U.S. Pat. No. 6,208,894, Schulman describes a network of neural stimulators and recorders implanted throughout the body communicating wirelessly with a central control unit. U.S. Pat. No. 6,522,928, Whitehurst, describes an improvement on the system described in Schulman using function electro stimulation also know as adaptive delta modulation to communicate between the implanted devices and the central control unit.

The greatest dynamic range is achieved by setting the minimum stimulation at the threshold of perception and the maximum stimulation level approaching the pain threshold. It is unpleasant for a subject to first concentrate to detect the minimum perception and then be subjected to stimulation near the threshold of pain.

One major concern in the field has been that the amount of electrical charge needed to elicit light percepts might be too high to permit long-term stimulation without damage to the retina. A second concern is that the current required to elicit percepts may fluctuate over time, due to either neurophysiological change or damage to the retina itself, electrochemical changes on the electrode surface, or instability of position of the array on the retinal surface.

Previous short-term acute studies (lasting less than 3 hours) found that localized retinal electrical stimulation of blind subjects with RP and AMD resulted in discrete percepts, however the amount of electrical current required to elicit a response was relatively large compared to animal studies examining retinal responses to electrical stimulation. One likely explanation for these high thresholds is that it is extremely difficult to lay an electrode array flush on the retinal surface during an acute trial. However an alternative possibility was that the high electrical thresholds found in human trials were due to the effects of retinal degeneration which include both loss of cells and severe rewiring within the inner layers of the retina.

The human retina includes about four million individual photoreceptors. An effective visual prosthesis may include thousands of electrodes. An automated system is needed to adjust individual electrodes in a visual prosthesis for maximum benefit without the need for subject interaction in a long and difficult process.

SUMMARY OF THE INVENTION

The invention is a method of automatically adjusting an electrode array to the neural characteristics of an individual subject. The response to electrical neural stimulation varies from subject to subject. Measure of impedance may be used to predict the electrode height from the neural tissue and, thereby, predict the threshold of perception. Alternatively, electrode height may be measured directly to predict the threshold of perception. Also, impedance measurement may be used to quickly identify defective electrodes and proper electrode placement.

BRIEF DESCRIPTION OF THE DRAWINGS

FIG. 2b is a Cross-sectional OCT image of the retina and electrode array shown in FIG. 2a.

FIG. 4 a-f are a set of six bar graphs showing perception threshold measurements in six subjects.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
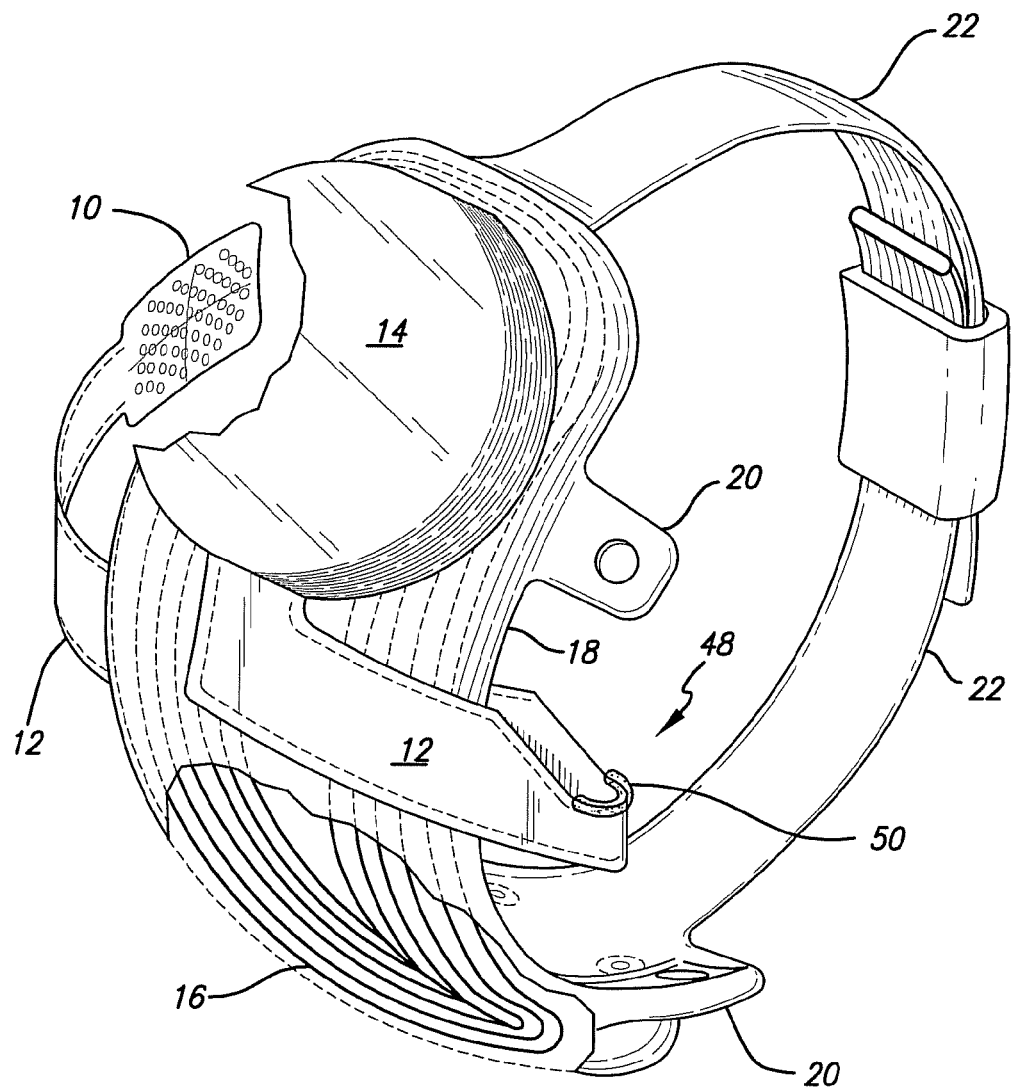
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

The preferred prosthesis includes an external portion (not shown) which includes a camera, video processing circuitry and an external coil for sending power and stimulation data to the implanted portion.

The electronics package 14 converts a radio frequency signal into electrical stimulation patterns. Input signals are provided via an inductive wireless link using an external antenna magnetically aligned over the secondary inductive coil 16. The desired pulse pattern is sent to a custom-built video processing unit that codes the data as a serial data stream, and transmits it to the implant via the wireless link. In addition, the transmitted signal supplied power to the implant. A reverse telemetry function in the implant allows direct measurement of impedance of each electrode. The subjects' un-operated eye is patched during all tests to ensure that subjects' thresholds are not affected by residual vision in the un-operated eye. While 1 kHz is used in the preferred embodiment, it should be noted that higher frequencies produce more accurate results. 1 kHz is a compromise between impedance accuracy and hardware complexity. It is further possible to determine impedance by a single biphasic pulse. Pulses may also take various wave forms such as sinusoidal or square wave.

Optical Coherence Tomography (OCT)

Optical coherence tomography may be used to measure the distance of the electrode array from the retinal surface and to measure retinal thickness. The underlying principle of OCT imaging is much like that of ultrasound, except that light is used instead of sound, thus permitting measurements resolved to the scale of ≤10 μm. Cross-sectional images of retinal tissue across multiple depth planes may be inferred from the profile of near infra-red backscattered light.

Figure 2A:
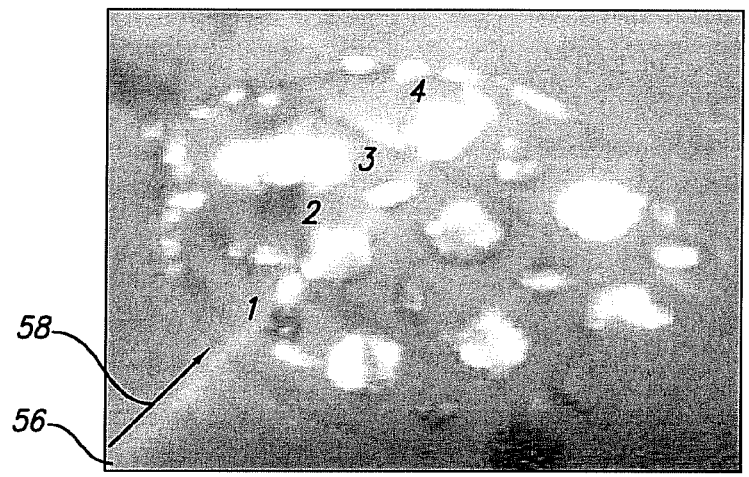
FIG. 2a is a fundus photo showing and electrode array on the retina.
Figure 2B:
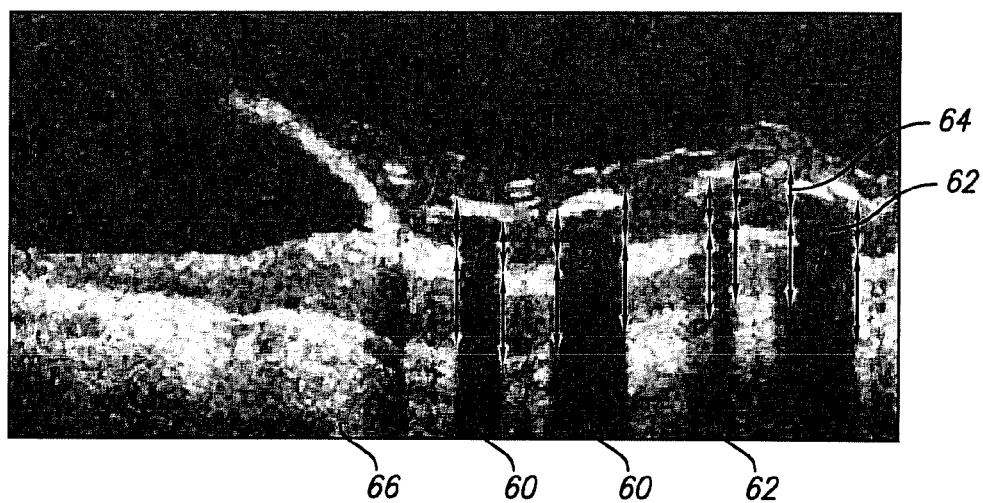

FIG. 2*a* shows a fundus image of an intraocular stimulating array with the OCT imaging light source visible 56. The arrow 58 represents the direction along which imaging is carried out. FIG. 2*b* shows the image of the cross-section of the retina that lies under the OCT imaging light source of 2*a*. Broad shadows are cast by the electrodes 60, and narrow shadows 62 are either due to the imaging light source passing across the edge of the electrode (as is the case in electrode 3 in this example) or are cast by individual wires within the array (note that wires also pass above individual electrodes). Corresponding electrodes are labeled across the figure. The small deviation between the fundus and OCT image is due to small eye-movements in the very short time interval that separates acquisition of the two images.

As shown in FIG. 2*b*, the distance of the electrode array from the retinal surface is defined as the distance from the top of each electrode to the inner surface of the ganglion cell layer arrows 64. Measurements therefore include the electrode thickness, which varies between 80-120 μm depending on the exact cross-section of the electrode over which the OCT measurement is taken. The thickness of the retina is defined as the distance from the inner surface of the retinal pigment epithelium to the surface of the internal limiting membrane 66.

As can be seen in FIG. 2, it was not always easy to determine the exact position of the top of the electrode, the surface of the internal limiting membrane, or the inner surface of the retinal pigment epithelium, and these judgments relied heavily on the experience of the experimenter. Two experimenters performed these analyses with the help of custom software written in Matlab. Such subjective measures could be automated through computer imaging and image recognition software to make this subjective measure objective.

Figure 3A:
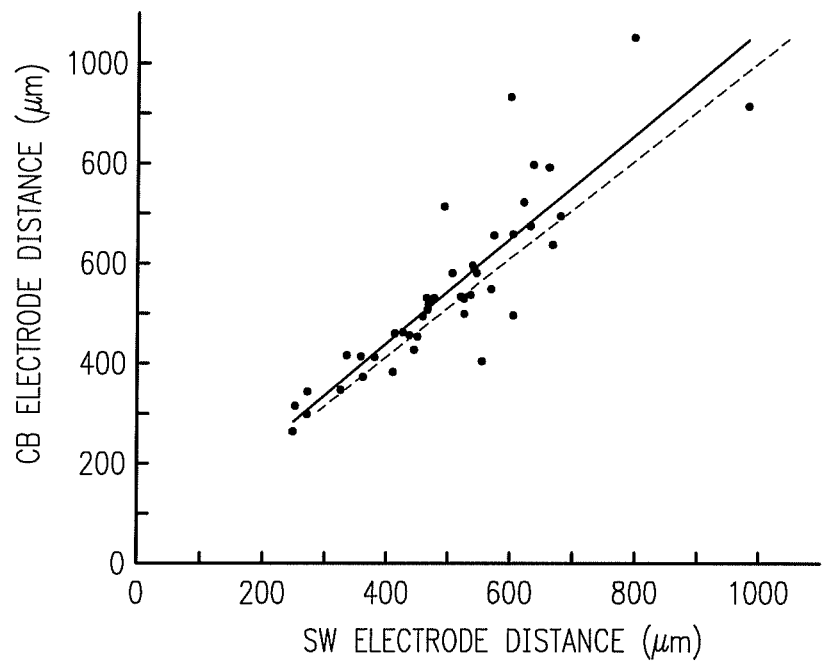
FIG. 3a is a graph showing OCT distance estimate by two observers.

We cross-validated the judgments of these experimenters by having both experimenters analyze the same subset of 43 estimates of electrode distance and retinal thickness. FIG. 3*a* plots the first experimenter's judgments of electrode distance from the retinal surface along the x-axis, and the second experimenter's judgments along the y-axis. If two experimenters' judgments were perfectly correlated the data would fall along the dashed line of slope 1. The actual best fitting regression line had a slope of 1.06, as shown by the solid line. A Monte-Carlo procedure in which each judgment was randomly assigned to an experimenter is used to assess whether the best-fitting regression slope for these data differed significantly from 1. Performance across observers was strongly correlated ($r^2$=0.78; $p<0.01$) and the difference between the best-fitting regression line and a line of slope 1 was not significant ($p>0.05$, two-tailed).

Figure 3B:
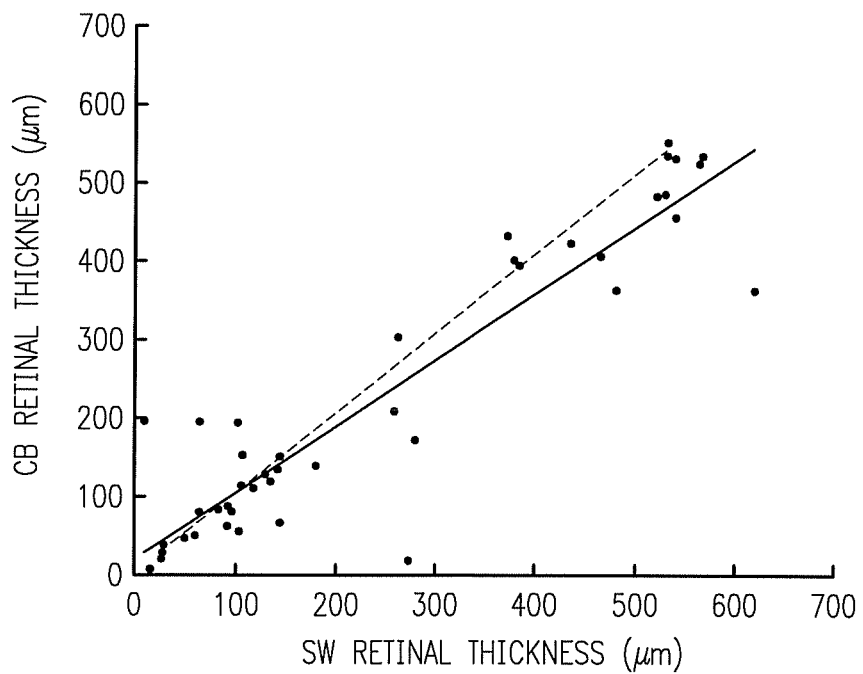
FIG. 3b is a graph showing OCT retinal thickness estimates by two observers.

FIG. 3*b* plots the first experimenter's judgments of retinal thickness along the x-axis, and the second experimenter's judgments along the y-axis. Once again, if the two experimenters' judgments were perfectly correlated the data would fall along the dashed line of slope 1. The actual best fitting regression line had a slope of 0.83, as shown by the solid line. Once again, performance across observers was strongly correlated ($r^2$=0.85; $p<0.01$) and a Monte-Carlo procedure demonstrated that the best-fitting regression slope did not differ significantly from 1 (p>0.05, two-tailed).

These measurements demonstrate that inter-experimenter differences in measurement between experimenters were small, and are unlikely to result in large errors or biases in estimates of either electrode distance or retinal thickness. The high consistency across experimenters demonstrates that trained observers can make consistent judgments about electrode distance and retinal thickness on the basis of our OCT images.

Impedance

Electrode impedance provides a measure of current resistance that is affected by both the electrochemical properties and size of the electrode itself, and the properties of the tissue surrounding the electrode. We can determine, in retinal implants, that impedance is associated with array position on the retinal surface. In particular, impedance is inversely proportional to electrode height. Note that electrode height as used herein refers to the distance between the retinal surface and the electrode.

Impedance is measured using software with a back telemetry program. The software uses a same diagnostic function of the implant by sequentially generating a 1 kHz, 10 µA sine wave on each electrode, recording the resulting voltage drop, calculating the impedance modulus in k$\Omega$ and transmitting this information from the implant to the external system via a reverse telemetry link. Impedance measurements are taken at the beginning and the end of each stimulating session and may be taken during surgery.

Perceptual Thresholds

Perceptual thresholds are the amount of current needed to detect a pulse on 50% of trials, corrected for false alarms, i.e. the amount of current needed to elicit visible percepts of light. We can measure detection thresholds for each electrode using a "standard pulse" consisting of a charge-balanced 0.975 ms cathodic pulse followed by a 0.975 ms anodic pulse with a 0.975 ms inter-pulse delay between cathodic and anodic components. All pulse waveforms were biphasic charge balanced.

During this period a yes-no procedure was used, with half the trials being blank trials. The stimulation intensity of the test pulse was varied using a three-up-one-down staircase, and each threshold was based on approximately 100 trials (generally 50 trials are adequate to estimate threshold with reasonable accuracy). After November 2004 this procedure was automated, and subjects responded whether or not they saw a stimulus on each trial via key press.

We validated that each change in procedure did not lead to a discernable change in estimated thresholds by measuring threshold using both the old and new technique on a number of electrodes before changing our protocol to the new technique.

Results

Thresholds

Phosphene appearance near threshold is typically white or yellow, and phosphenes are reported as being round or oval in shape. In these cases an increase in the stimulation current results in subjects seeing a light spot in the same location. Phosphenes at threshold were not uncomfortable or unpleasant.

Mean thresholds over the entire period over which we collected data for each subject are shown for each electrode and subject in FIG. 4. For each subject, electrodes are ordered from least to most sensitive along the x-axis. Gray and black bars represent electrodes with a diameter of 250 and 500 µm respectively. Threshold current required for the subject to see a pulse on 50% of trials corrected for false alarms is shown along the y-axis. Note the dramatic change of scale along the y-axis across subjects. Most of the variation in threshold across repeated measurements (single error bars are shown) is due to variation in threshold over time as opposed to measurement error, as illustrated in FIG. 6; measured thresholds taken within a few days of each other tend to be very close in value.

Thresholds as a Function of Electrode Size

Figure 5A:
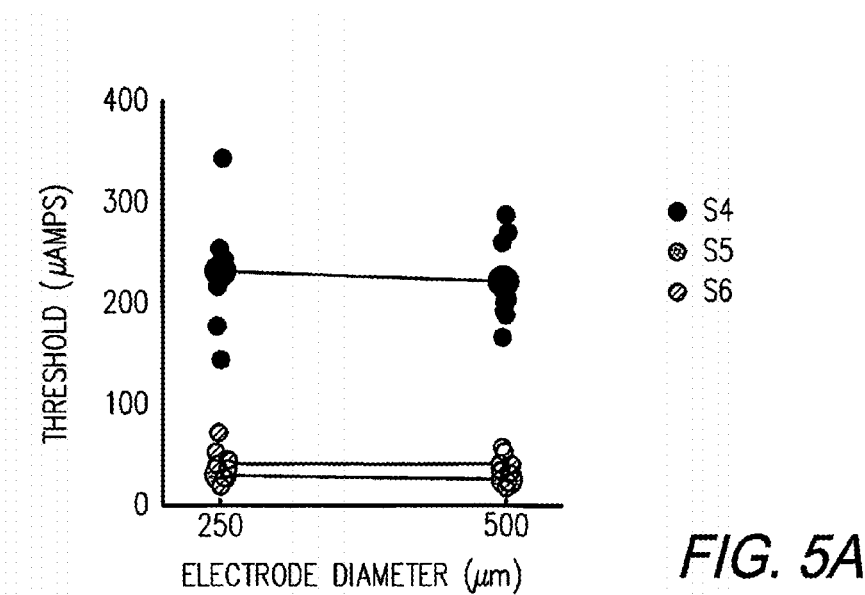
FIG. 5 a-c are graphs showing the relationship between electrode diameter and threshold of perception.

Subjects S4-6 were implanted with checkerboard arrays in which electrodes of 250 and 500 µm alternated in the array (see FIG. 2*a*). We compared mean threshold between these two electrode sizes for each subject. Other data shown suggest that the distance of the array from the retinal surface has a dramatic effect on thresholds. However, the checkerboard arrangement used in these three subjects provided a way of crudely factoring out the effects of electrode distance, since any variation in the distance of electrodes was likely to average out across the two electrodes sizes. To our surprise, we found that electrode size did not affect current threshold (Two-factor, subject x electrode size, ANOVA, p>0.05 F=0.367), see FIG. 5*a*.

Figure 5B:
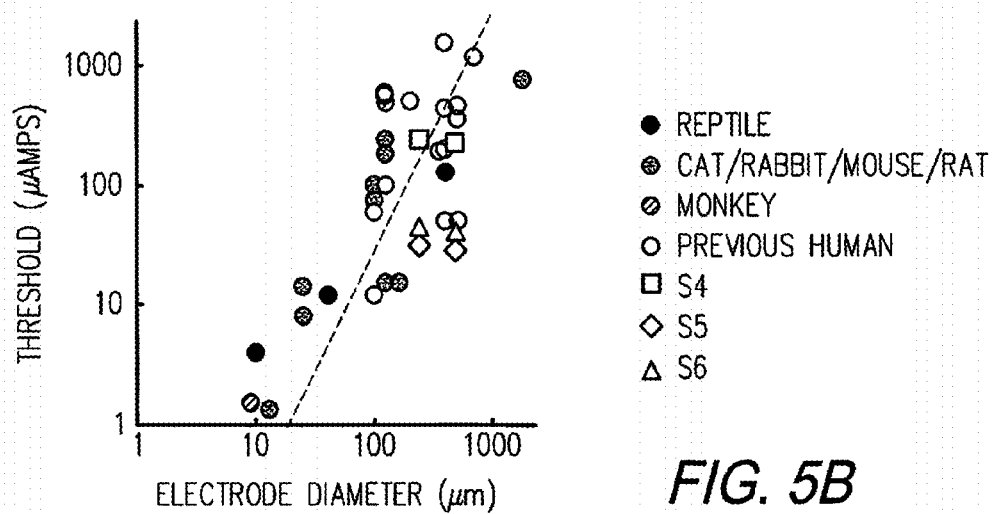

It has previously been shown within in vitro animal preparations that the log threshold current required to elicit spikes within in vitro retina is linearly correlated with log electrode area. FIG. 5*b* compares mean thresholds. It is possible that a wider range of electrode sizes would make threshold differences as a function of electrode size more apparent. It is also possible, given the large electrode sizes used in this experiment that current density is highest in a ring around the electrode edges. Smaller electrodes would be expected to have more even current distribution across the electrode surface.

As illustrated in FIG. 5*b*, previous human studies, which were mainly carried out in acute preparations, show remarkable variability in threshold. There are multiple potential causes for this variability. Under acute conditions subject concentration and electrode position are difficult to control and it is only possible to collect a small number of trials. Even where data were collected chronically, reported thresholds were based on a small number of trials, and different sizes of electrodes were not implanted within the same subjects, thereby confounding array position and inter-subject variability with electrode size.

The data reported here are lower than those reported in previous studies, and demonstrate that the current intensity levels required to elicit percepts in humans are consistent with the current intensities required within in vitro experiments using similar electrode sizes. Our subjects are surprisingly sensitive, given that the criterion used to define threshold used within in vitro studies is current stimulation level will reliably elicit spike in a single cell. However it has been previously shown that subjects with normal vision can reliably detect a single photon of light, suggesting that a very small increase over the baseline firing rate of ganglion cells is probably sufficient to mediate behavioral detection. It is also possible that degenerated human retina is more sensitive to electrical stimulation than the non-degenerate rodent retinal models generally used for in vitro experiments.

Thresholds Over Time

Thresholds do not remain stable over time, as shown in the first column of FIG. 6. On the whole, subject thresholds tended to increase postoperatively, consistent with the electrode array lifting off the retina. For each subject we calculated the best-fitting linear regression over time across all electrodes. As described above, S2's array separated from the retina after 11 months due to the subject falling and bumping her head and the array was then reattached. For this subject we calculated separate linear regressions for each array attachment.

In all subjects except S1 there was a significant tendency for the slopes of the linear regression describing threshold as a function of time for each individual electrode to have a positive slope (two-tailed t-test, p<0.05). For S1 the tendency for slopes to be positive fell just below significance (p=0.057, t=2.061). While reasonably well fit by a linear regression, each subject showed individual patterns of threshold instability over time. As discussed below, we believe that these changes in threshold are mainly driven by changes in the distance of the electrode array from the retinal surface.

Impedances

Figure 5C:
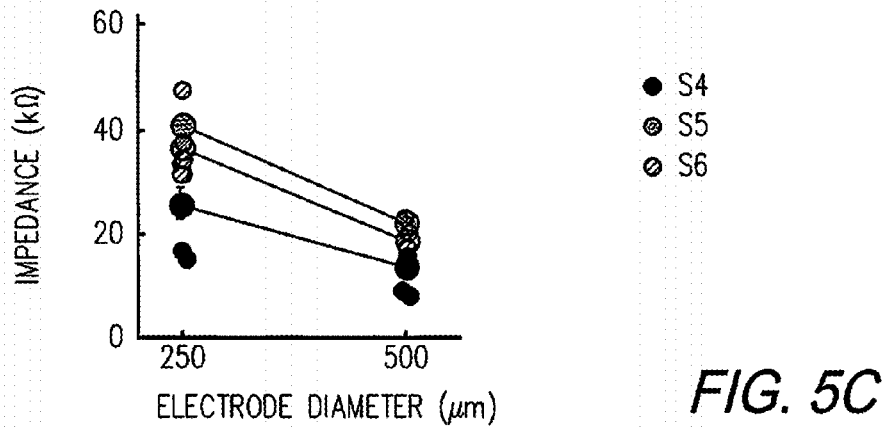
Figure 6B:
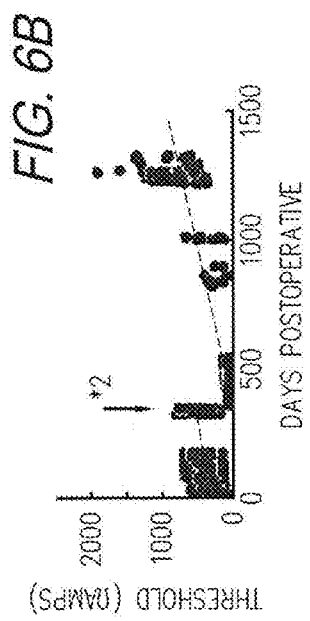
FIG. 6 a-v are graphs showing the relationship of time to threshold of perception, impedance, electrode height, and retinal thickness.
Figure 6A:
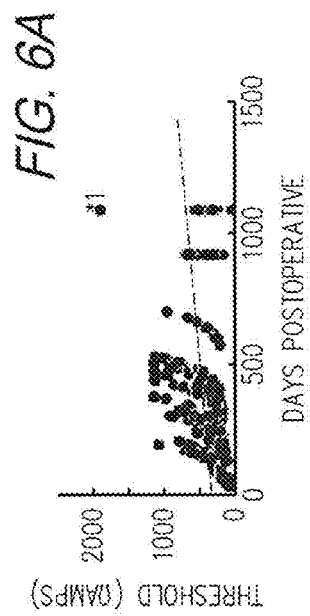
Figure 6D:
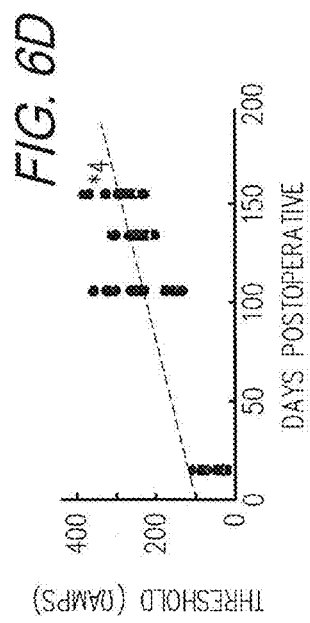
Figure 6C:
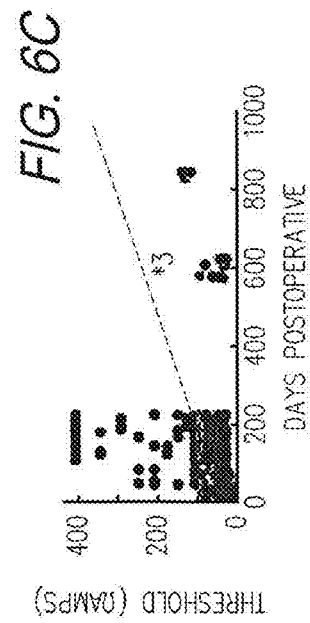
Figure 6F:
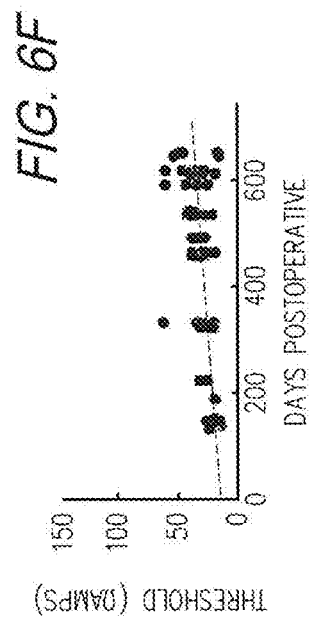
Figure 6E:
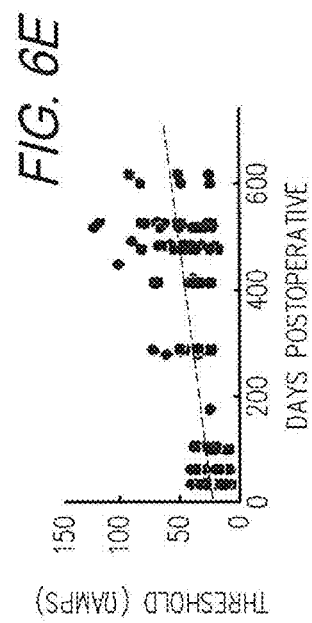

As would be expected, impedance did vary with electrode size, as shown in FIG. 5c (Two-factor ANOVA with replication, (p<0.001, F=146.650). After implantation we also see significant variability in impedance over time, as shown in the second column of FIG. 6. On the whole, subject impedances tended to decrease postoperatively during the weeks and months after implantation, consistent with the electrode array lifting off the retina. These data, together with that from OCT measurements, suggests that for the relatively thick and heavy arrays used in this implantation a single tack was not sufficient to maintain the array in a stable position flush to the retinal surface.

For each subject we calculated the best-fitting linear regression over time across all electrodes. For all subjects except S5, the slopes of the linear regressions describing impedance as a function of time for each electrode had a significant tendency to decrease over time (p<0.05). For S5 there was a non-significant tendency for slopes to be negative (p=0.122, t=−1.6416). While reasonably well fit by a linear regression, each subject showed an individual patterns of impedance instability over time. As discussed below, we believe that these changes in impedance are mainly driven by changes in the distance of the electrode array from the retinal surface.

Array Position and Retinal Thickness

The two right columns of FIG. 6 show measured distances of the array form the retinal surface and measured retinal thickness respectively. Note that estimates of electrode distance from the retina include the thickness of the electrode (approximately 80-120 µm), as described in Methods above. Occasionally there were multiple OCT images of the same electrode taken on the same day. In these cases measurements of electrode distance and retinal thickness for that electrode were averaged and standard errors calculated. Due to the difficulty in collecting these measurements, only a subset of electrodes were measured on any given date. No clear trend over time is visible across subjects for either electrode distance or retinal thickness.

The Relationship Between Threshold, Impedance, Electrode Distance and Retinal Thickness.

FIG. 7a-f shows the relationship between threshold, impedance, electrode distance and retinal thickness. In all cases data are plotted on log-log axes. To find corresponding measurements, we partitioned our data into 30 day time periods. So for example, a given data point comparing impedance and threshold values might represent the average across several impedance measurements and several threshold measurements both collected within the same 30 day time period (e.g. post-operative days 50-79 inclusive). All data within FIG. 7 are based on the same 30-day time window approach. Data therefore include repeated threshold and impedance measurements on each electrode. Electrode height and retinal thickness measurements were taken less frequently, but the same approach still applied; electrode height and retinal thickness estimates were compared to impedance or threshold measurements taken within the same 30 day time window as the OCT measurement.

Figure 7A:
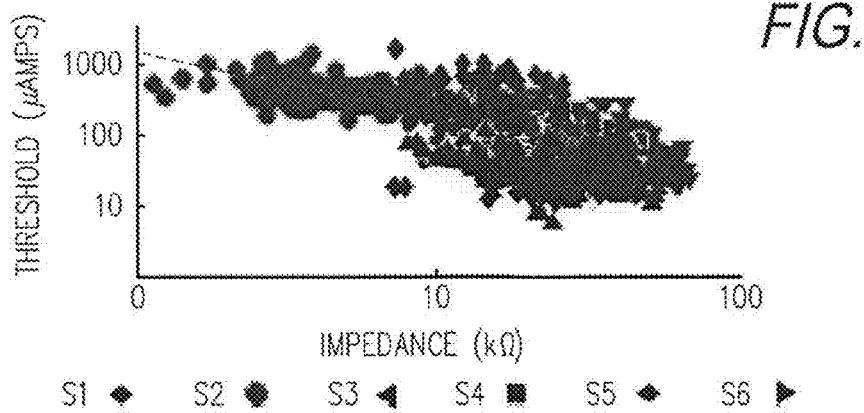
FIG. 7 a-f are graphs showing the correlation of threshold of perception, impedance and retinal thickness.

As shown in FIG. 7a, across subjects there was a significant slope (s) of −1 (s=−1.0, p<0.001) between threshold and impedance. (log threshold=1/log impedance+k) on log axes. The linear regression slope on log-log axes was significantly less than zero in 5 of the 6 individual subjects (S1, s=−14.1, p<0.001; S2, s=−15.8, p<0.001; S3, s=−4.4, p<0.001; S4, s=−6.15, p<0.001; S6, s=−0.578, p<0.001).

Figure 7B:
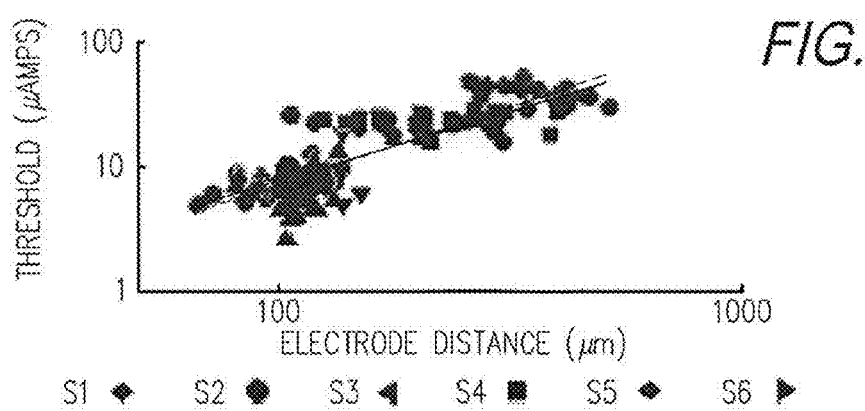

As shown in FIG. 7b, across subjects there is a positive correlation between log electrode distance from the retina and log threshold (s=2.21, p<0.001). However the slope was significantly greater than zero in only 1 of 5 of the individual subjects for which OCT data were available (S2, s=1.954, p<0.001). There was, therefore, a strong relationship between estimated electrode distance and threshold across subjects, but this correlation was not apparent within individual subjects.

It has been suggested that, in retinal stimulation, the electric field may diminish with the square of the distance from the electrode, as occurs in an isotropic medium with distant boundaries. If so, thresholds should increase with the square of the distance of the electrode from the retinal surface. Recent electrophyiological data do indeed find that spike thresholds increase with distance according to a square law within in vitro retinal preparations. The solid line that overlaps the best-fit dashed line shows predicted regression based on the square of the distance (the intercept was minimized using a maximum likelihood procedure). The good fit suggests that, for our array configuration, modeling the electric field current as an isotropic medium with distant boundaries may provide a reasonable model for electrical stimulation thresholds.

Figure 7C:
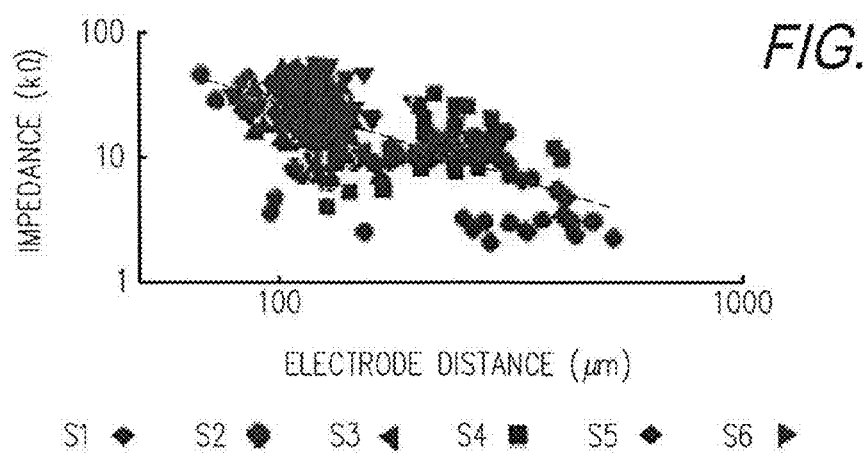

As shown in FIG. 7c, across subjects there is negative correlation between log impedance and log electrode distance (s=−1.1, p<0.001). The linear regression slope on log-log axes was significantly less than zero in only 2 of the 5 individual subjects for which OCT data were available (S2, s=−0.08, p<0.001; S6, s=−0.3, p<0.001). Therefore there was once again a strong relationship between estimated electrode distance and impedance across subjects, but this correlation was again not clear within individual subjects.

Figure 7D:
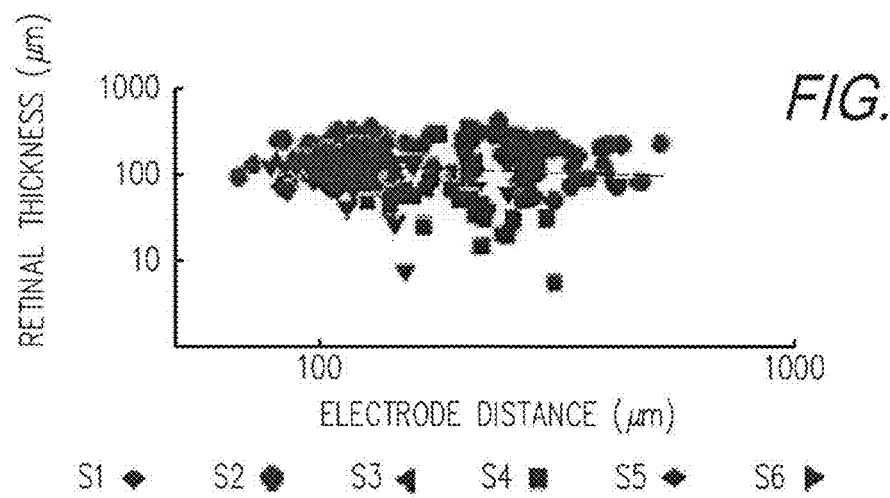

As shown in FIG. 7d, there was a very shallow but significant negative correlation between electrode distance and retinal thickness (s=−0.18, p<0.05, note that this significance level does not remain significant after correction for multiple comparisons) across subjects. One possible explanation for this weak correlation may have been that the surgeon may have been more conservative in the placement of the array in subjects whose retinal surface appeared more fragile. S5 showed a significant positive slope relating electrode distance from the retinal surface and retinal thickness (S5, s=1.213, p<0.01, p<0.05 after Bonferroni correction), which may have been due to a slight compression of the retinal surface by the array in this subject. Alternatively it is possible that the high currents that are necessary when there is a large distance between the array and the retina resulted in a reduction of the thickness of the retinal surface.

Figure 7E:
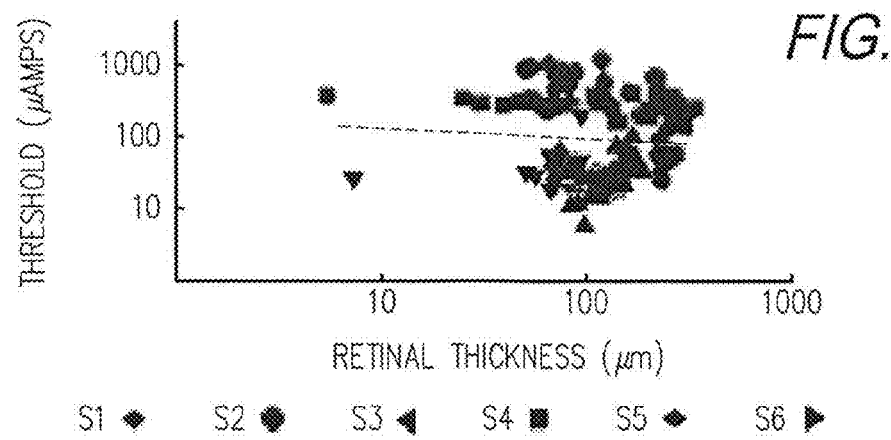

As shown in FIG. 7e, across subjects there was no correlation between retinal thickness and impedance (p<0.05). Within the 5 individual subjects, two subjects had a shallow negative correlation (S3, s=−0.3, p<0.001;

S6, s=−0.1, p<0.001) and a third showed a shallow positive correlation (S4, s=0.04, p<0.001).

Figure 7F:
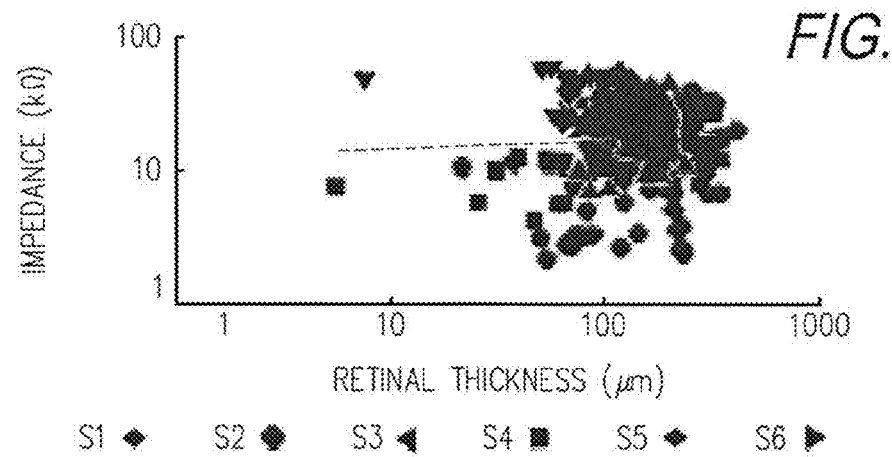

As shown in FIG. 7f, across subjects there was no correlation between retinal thickness and threshold (p<0.05). One subject showed a significant positive correlation (S6, s=0.4, p<0.01). These leftmost three figures (d, e, f) suggest that there was little compression of the retina by the array, and what compression there was did not have a major affect on either thresholds or impedance.

Discussion

Consistent with the hypothesis that the high thresholds reported in previous human acute studies were due to distance between the electrode array and the retinal surface, we find that our thresholds are significantly lower than had been previously reported for human retinal electrical stimulation. Indeed, in our later subjects electrical stimulation thresholds are comparable to those reported in the animal in vitro electrophysiological literature. This suggests that retinal degeneration due to RP does not result in a significant elevation of the electrical stimulation threshold.

We found that thresholds were the same for 250 and 500 µm electrodes. This is in contradiction to a recent literature review by Sekirnjak et al. who found, across a wide range of in vitro and in vivo studies, that log thresholds increase linearly with log electrode area, with a slope of 0.7. However, as shown by FIG. 5b, it is possible that a wider range of electrode sizes would make threshold differences as a function of electrode size more apparent. It is also possible, given the large electrode sizes used in this experiment that there was a "ringing" of current around electrode edges. Smaller electrodes would be expected to have more even current distribution across the electrode surface.

Here we simply measured threshold: the current needed for stimulation to be reliably detected. Useful prosthetic vision will, of course, require supra-threshold stimulation at higher current intensities that are needed to elicit a threshold percept. Nonetheless, thresholds provide a useful indication of the lower limit beyond which it will be difficult to reduce electrode size. Our low threshold values suggest that even without any reduction in threshold current amplitude with smaller electrodes (as would be predicted from in vitro data, see above), it may still be possible to use smaller electrodes than those used in this study provided the array is close to the retinal surface. The results from S5 and S6 (where the surgeon was more experienced with tacking the array to the retinal surface) both show thresholds consistently below 100 µA (1 ms pulse) on a majority of the electrodes. Assuming platinum has a conservative safe stimulation limit of 0.10 $mC/cm^2$, these data imply that an electrode of just under 200 µm diameter would be acceptable. More advanced materials such as iridium oxide, with higher safe stimulation limits could safely permit an electrode of 65 µm diameter. Reducing electrode size will permit more electrodes within the same retinal area, translating into more pixels per degree of visual angle. Simulations of prosthetic vision suggest that more electrodes in the central visual area of the retina may lead to a higher resolution image and better visual task performance.

Our data confirms in vitro retinal electrophysiology data suggesting that the distance of electrode from the retina is a significant concern. We see a positive correlation between threshold current and electrode distance from the retina (with a slope consistent with the hypothesis that the electric field may diminish with the square of the distance from the electrode). This suggests that stimulus current requirements are likely to increase significantly as the electrode lifts off the retina, resulting in large power consumption by the stimulator and a need for significantly larger electrodes to safely supply current. A second concern is that the ability to produce small localized percepts is also likely to be compromised by large separations between electrodes and the retinal surface.

We see a negative correlation between electrode distance and impedance, consistent with the notion that electrodes that are flush on the surface of the retina have higher impedances (due to the adjacent retinal tissue) than electrodes that have lifted from the retina (where saline solution intervenes between the electrode and the retinal surface).

We believe that the distance of electrodes from the retinal surface is similarly the common factor responsible for the negative correlation between threshold and impedance. Correlations between threshold and impedance were significant in 5 out of the 6 individual subjects. We believe finding significant correlations within individual subjects between threshold and impedance but not for OCT measurements likely to be due to the fact that we had a much larger data set for impedance and threshold values (OCT data were sparse due to collection difficulties).

The relationship between electrode distance from the retinal surface, impedance and threshold can been seen very clearly in S2, FIG. 6. A lifting of the array (observed using fundus imaging since OCT imaging was not available at the time) led to an increase in thresholds and a decrease in impedances. After the array was reattached impedances increased and thresholds dropped. There was then a second gradual lifting of the array from the retinal surface, which was again accompanied by an increase in thresholds and a decrease in impedance.

We see an initial instability in impedance values shortly after implantation and stimulation that may be analogous to the rapid changes in impedance due to changes in the tissue surrounding the electrode and electrochemical changes within the electrode that are found in cochlear implants. However, because OCT measurements were only taken at relatively infrequent intervals we cannot exclude the possibility that these changes in impedance were due to slight shifts in the position of the array as it 'settled' on the retina.

If long term stimulation led to retinal tissue damage or electrode corrosion we might expect to see gradual increases in thresholds and changes in impedance that were not associated with changes in the position of the array. In subjects S4 and S6 OCT measurements were taken over an extended time period during which the array remained stable. During this time period changes in threshold and impedance values tended to be relatively small (see FIG. 6). However it is nonetheless possible that that there may be subtle postoperative changes in either the electrode surface or the retinal surface underlying the electrode that were not apparent in our data.

As better OCT imaging techniques become available it may be feasible, in the next generation of retinal implants, to track short term changes in electrode distance to the retina in the immediate post-operative period. Detailed information about the distance of the electrode from the retinal surface will allow a much finer characterization of the relationship between threshold, impedance and electrode position during the immediate post-implantation period.

Our data demonstrate that maintaining close proximity between the electrode array and the retinal surface will be critical in developing a successful retinal implant. Thinner electrode structures may maintain more stable proximity to the retina will become more tractable. With the use of electrode arrays that are stable and flush on the retinal surface, and more complex measures of perceptual performance than our simple threshold measure, it is likely that other factors such as electrode size, retinal deterioration and subject age may begin to play a more significant role.

Hence, the applicant has determined through experiment that, for electrical stimulation of the retina, electrodes with high impedance require less current to create the perception of a pixel of light. This relationship varies with electrode size. Impedance values may therefore provide a quick measure of the sensitivity of an electrode (i.e. the amount of current needed to elicit a percept on that electrode).

Impedance also varies with the height of the electrode array from the retinal surface. This means that impedance measurements can be used to estimate whether the array has shifted on the retina, and to estimate the distance of various parts of the array from the retinal surface in a less time-consuming way that direct measurements of retinal position (such as OCT).

Threshold varies with the height of the array from the retinal surface. Therefore, if measuring the height of each electrode from the retinal surface is possible, it is possible to estimate electrode sensitivities based on their height from the retinal surface.

Impedance can also vary across the retinal surface due to disease and physical irregularities. It is advantageous to provide a surgeon with real time impedance information during surgery to aid the surgeon in placing the stimulating electrode array.

It should also be noted that it is not always necessary to test every electrode. As array resolution becomes greater, it will become increasingly difficult to test every electrode. Geographically related electrodes tend to have similar impedance, electrode—retinal height, and threshold of perception. Hence, impedance, electrode—retinal height, and threshold of perception can be extrapolated from testing sample electrodes.

Figure 8:
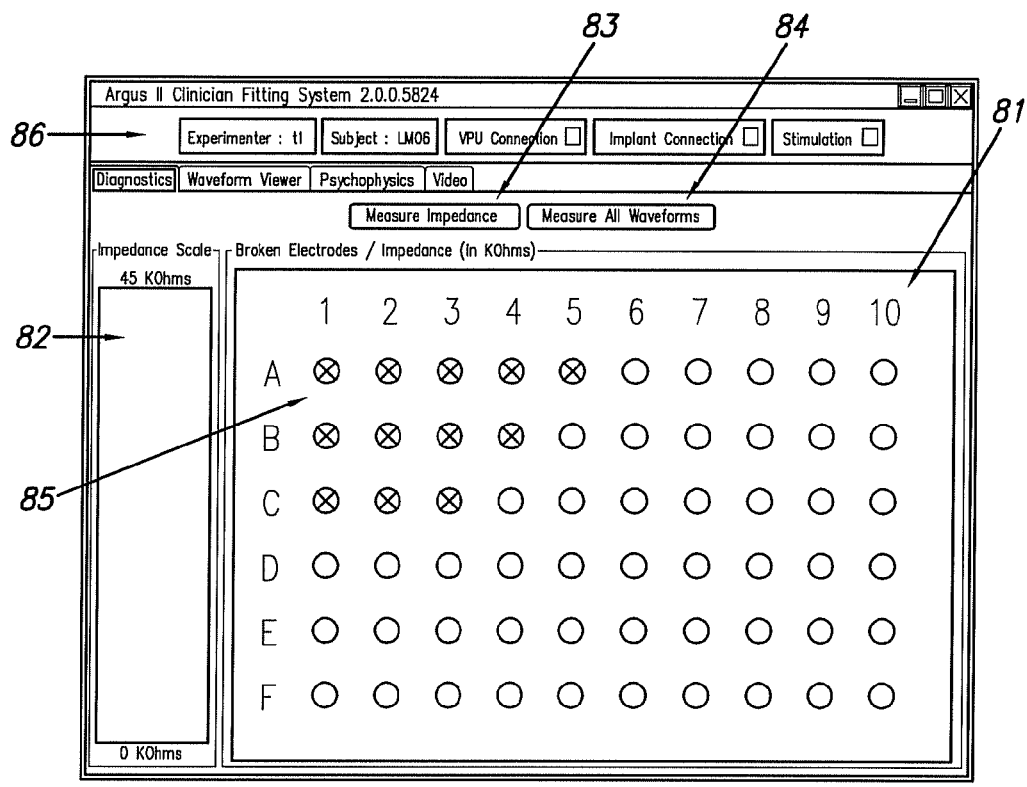
FIG. 8 depicts a screen showing the preferred method of communicating electrode impedance.

FIG. 8, depicts a computer screen optimized for providing impedance information in a clear and simple manner. The screen provides a grid of dots 81, one dot corresponding to each electrode. The dots on the computer screen are in the physical layout as the electrode array. A series of colors ranging through the color spectrum are assigned to impedance ranges and show in a key 82 to the left of the dots 81. Each time an impedance measurement is taken, the dot corresponding to the measured electrode is colored according to the measured impedance. After the entire array of electrodes have been measured, the physician can quickly scan the hue of the screen to assess the placement of the electrodes or any areas that have higher impedance than others. This allows the surgeon to quickly asses multiple locations while implanting an electrode array. Alternatively, an audible signal where pitch is proportional to mean frequency of the electrodes may allow a surgeon to look at the array placement while receiving impedance feedback.

It is also advantageous to further emphasize electrodes out of acceptable range by placing an X 85 across the corresponding dot. The measurement may be continuous or activated manually by a measure impedance button 83 on the screen. An all waveforms button 84, displays the complete stimulation wave form for analysis as described with respect to FIG. 11 below. The information screen also includes information 86 on the experimenter, subject, proper communications, and if the implant is currently stimulating.

The implanted neural stimulator provides bidirectional data through an RF link. Stimulation information is provided to the implanted device and telemetry information including voltage drops, from which impedance is calculated, is sent back. Impedance measurement is generally conducted sub-threshold. Although stimulation may be supra-threshold, it should be low enough to not disturb the subject. A stimulation current too small to create a percept, will still return a voltage drop measurement that can be used to calculate impedance using Ohms law.

Figure 9:
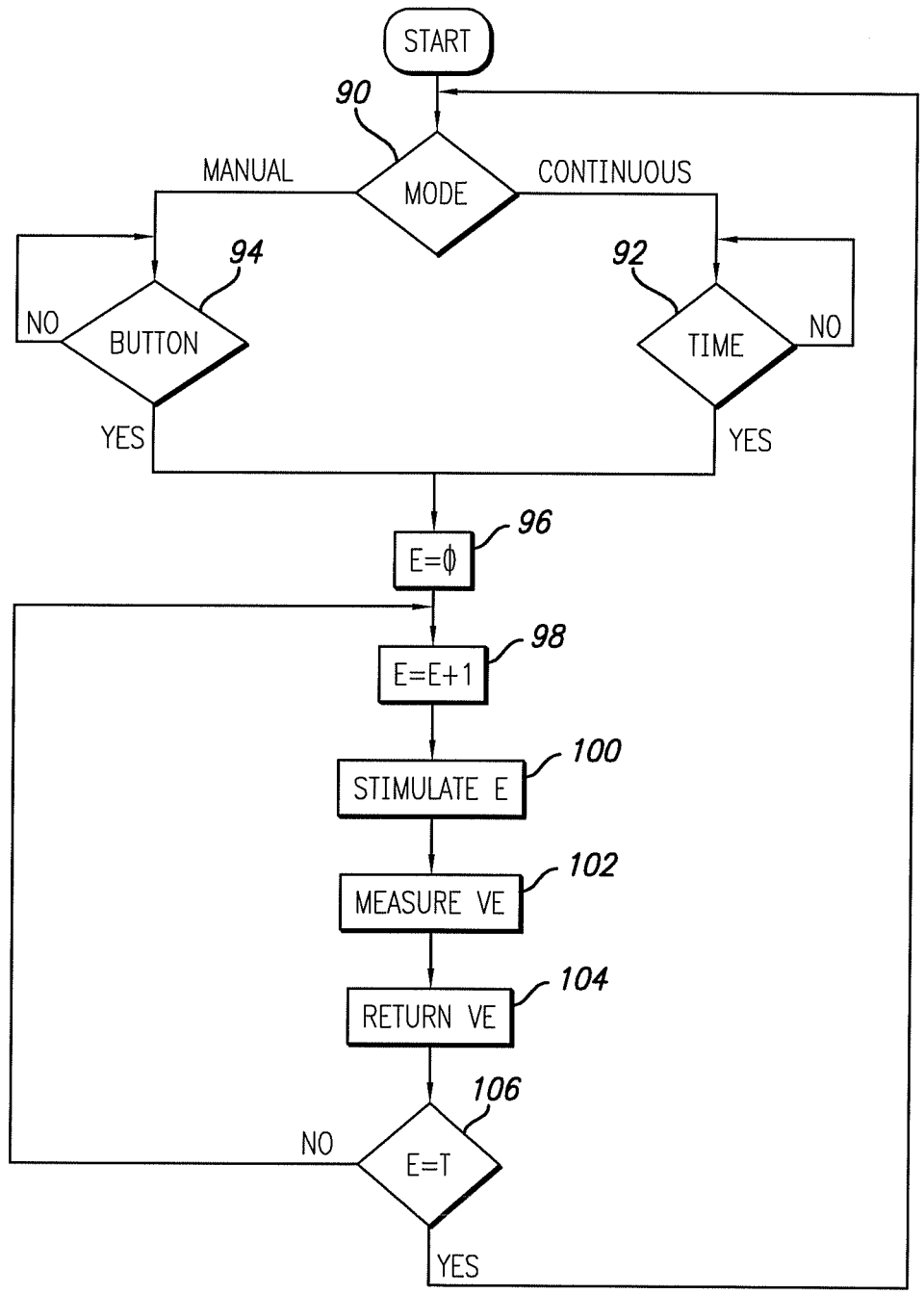
FIG. 9 is a flowchart of the impedance test.

FIG. 9 describes the testing procedure. As stated above, the testing can be automatically repeated or activated by the press of a button. Hence the testing software first determines the mode 90. In continuous mode the software continuously test a timer 92 for the next testing event. In manual mode, the software test for the press of the test button 94. Either will start the test cycle. First, the electrode counter E is set to 0 96, and incremented 98. Electrode E is stimulated 100 with a sub-threshold stimulation pulse. The voltage drop is measured 102 and returned to the external system 104. If E is not equal to the total number of electrodes 106, the process is repeated until it is. Upon measuring all electrodes the software returns to check the mode again 90.

Figure 10A:
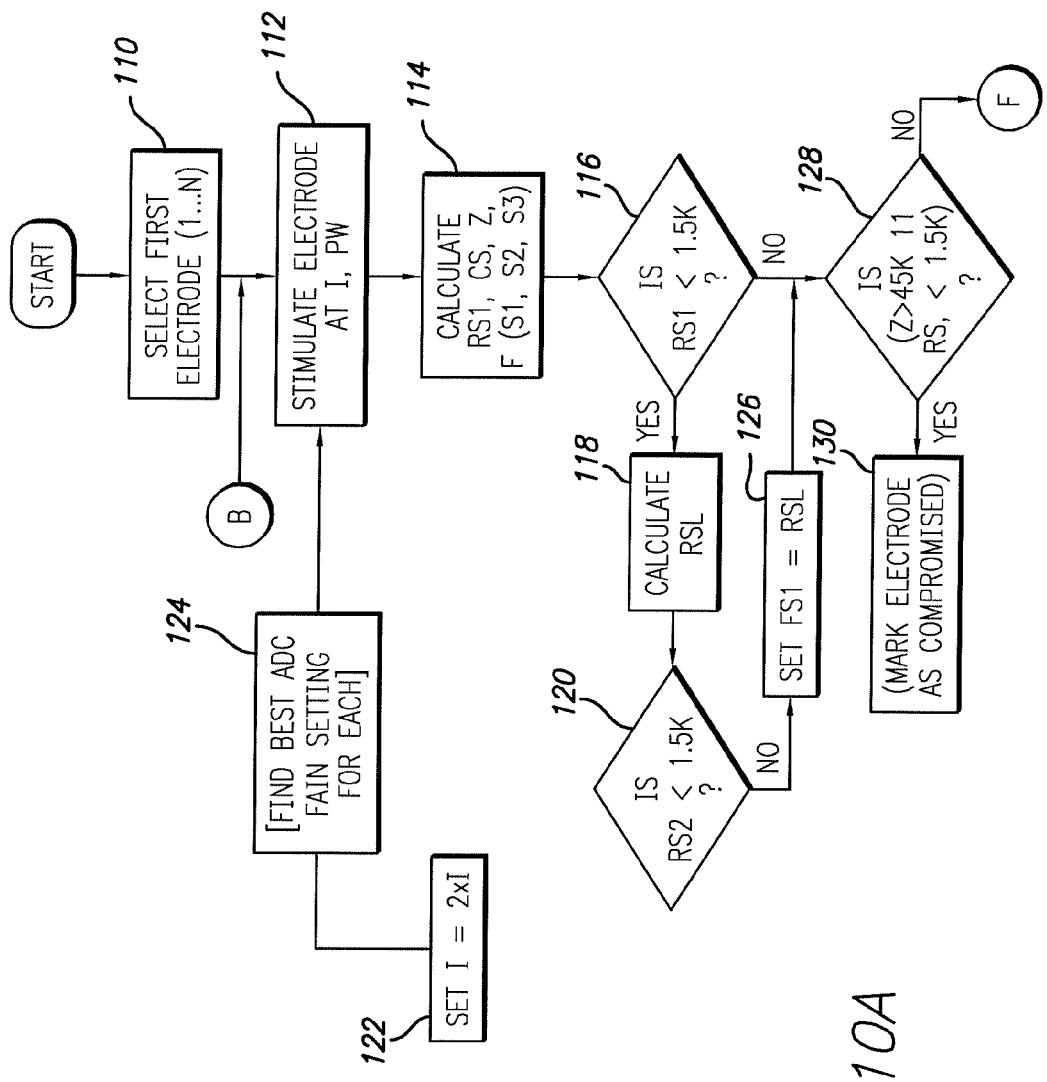
FIG. 10 *a-c* are a flowchart of the automated impedance measurement and electrode deactivation procedure.
Figure 10B:
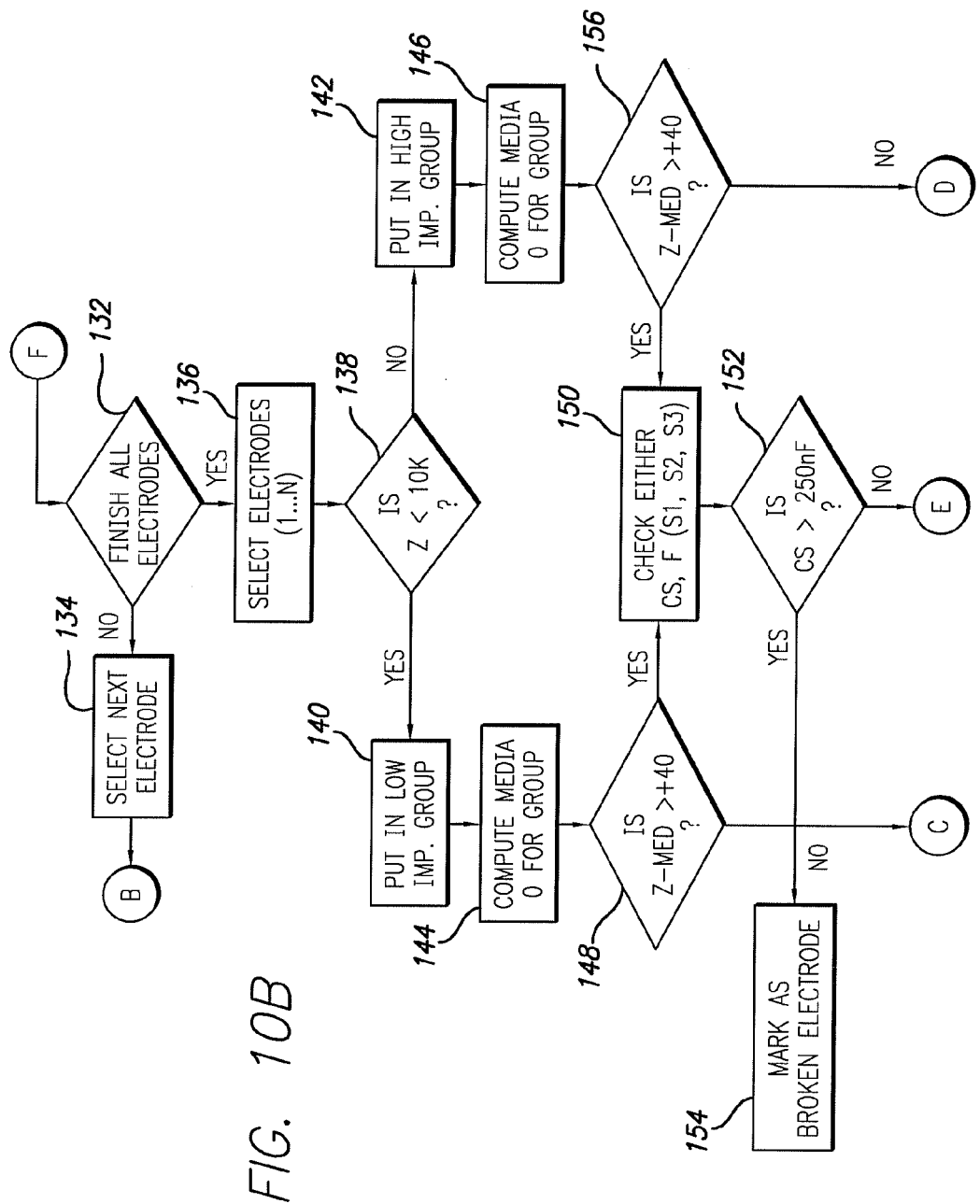
Figure 10C:
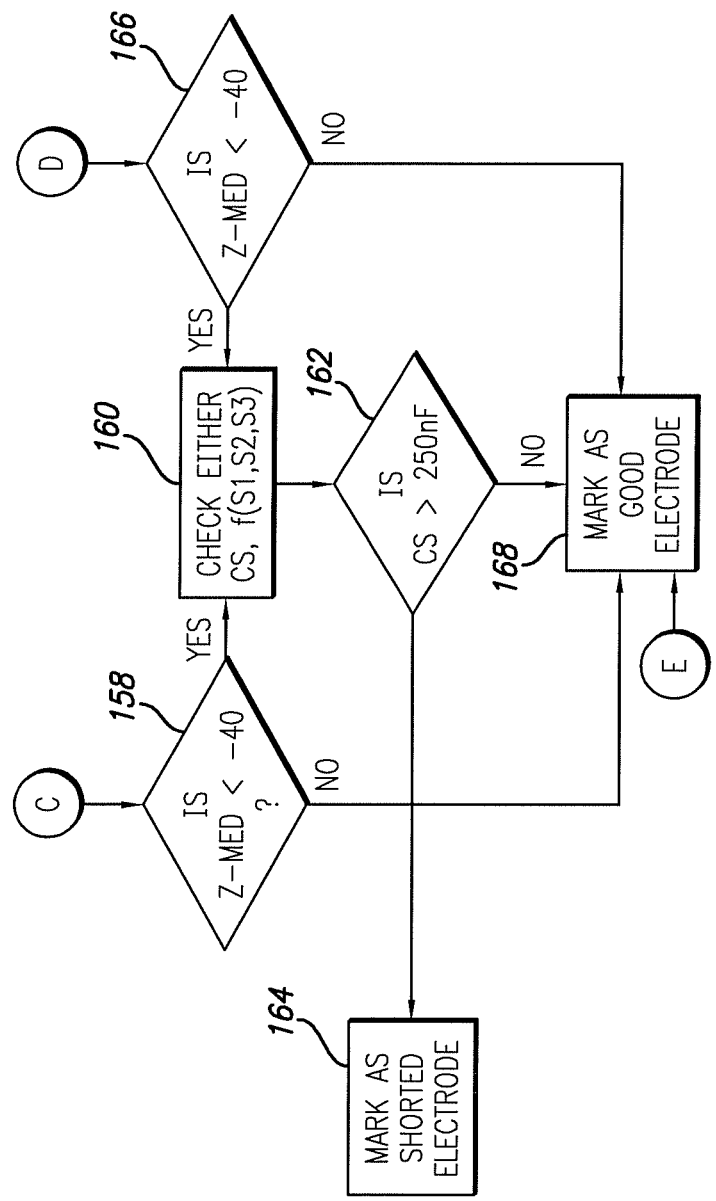

FIG. 10 shows a method of identifying defective electrodes by impedance and deactivating those defective electrodes. The process begins by selecting the first electrode 110. The selected electrode is stimulated at a predetermined current and pulse width after the best gain setting has been identified for that electrode 112. The system then performs the following calculations 114:

$$R_{S1}=v2-v_1/I;$$

$$C_S=(I*\text{pulse width})/v_5-v_2;$$

$$Z=(V_5-V_1)/I;$$

$$R_{S2}=V_5-V_6/I.$$

$f(S_1, S_2, S_3)$ which can be one of a number of functions include including linearity, monotonicity, or similar function. $V_{1-6}$ are voltage drops taken at various points in the stimulation waveform (see FIG. 11). S1, S2, S3 are the incremental slopes of the capacitive charging portion of the voltage measurement. If $R_{S1}$ is less that 1.5KΩ 116, the system calculates $R_{S2}$ 118. If $R_{S2}$ is less than 1.5 KΩ 120, current is doubled 122 and the best gain setting is found 124 and the electrode is stimulated again. This doubling of the measurement current is continued till it reaches the maximum charge density safety limit. When the current reaches the safety limit without a good measurement being obtained, the electrode is marked as compromised. If $R_{S2}$ is greater or equal to 1.5 KΩ, 120, $R_{S1}$ is set to $R_{S2}$ 126. If Z is greater than 45 KΩ and $R_{S1}$ is less than 1.5 KΩ 128 then the electrode is marked as compromised 130. If not all electrodes have been tested 132 then the next electrode is selected 134. If all electrodes have been tested 132, the process returns to the first electrode 136. If Z is less than 10 KΩ, 138, the electrode is marked as in the low impedance group 140. Otherwise it is marked as in the high impedance group 142. The system computes the median Z and standard deviation for the low impedance group 144 and the median Z and standard deviation for the high impedance group 146. If Z for an electrode minus the median Z is greater than or equal to four times the standard deviation 148, then calculate $C_S$ (or alternatively calculate the function of S described above and mark the electrode broken if the function pass criteria is violated) 150. If $C_S$ is greater than 250 nF 152, the electrode is marked broken 154. Alternatively, if an electrode is the high impedance group and Z for the electrode minus the median Z is greater than or equal to four times the standard deviation 156, then $C_S$ is calculated (or alternatively calculate the function of S described above and mark the electrode broken if the function pass criteria is violated) 150 and if $C_S$ is greater than 250 nF 152, the electrode is marked broken 154. Otherwise, the electrode is marked good 168.

If an electrode is in the low impedance group and its Z minus the median Z is less than the negative of four times the standard deviation 158, then calculate $C_S$ (or alternatively calculate the function of S described above and mark the electrode shorted and if the function pass criteria is violated) 160. If CS is greater than 250 nF 162, the electrode is marked shorted 164. Alternatively, if an electrode is the high impedance group and Z for the electrode minus the median Z is less than the negative of four standard deviations 166, then $C_S$ is calculated (or alternatively calculate the function of S described above and mark the electrode shorted and if the function pass criteria is violated) 160 and if $C_S$ is greater than 250 nF 162, the electrode is marked shorted 164. Otherwise, the electrode is marked good 168. Hence, a fully automated system can measure impedance, predict a fitting curve and identify defective electrodes without clinician intervention.

Figure 11:
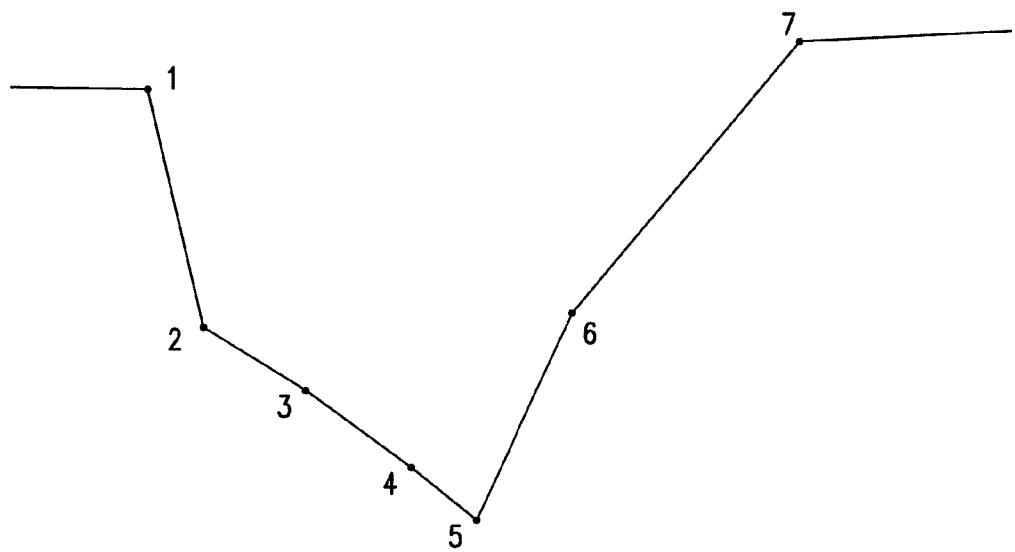
FIG. 11 depicts a stimulation pulse further illustrating the measurements described in FIG. 10.

FIG. 11 depicts a stimulation pulse further illustrating the measurements described in FIG. 10. Points labeled one through 7 are voltage measurement points. Hence $V_1$ is the voltage drop measured at point 1. $S_1$ is the slope of the curve between $V_2$ and $V_3$, $S_2$ is the slope of the curve between $V_3$ and $V_4$ and $S_3$ is the slope of the curve between $V_4$ and $V_5$ Accordingly, what has been shown is an improved method of making a neural prosthesis and improved method of stimulating neural tissue. While the invention has been described by means of specific embodiments and applications thereof, it is understood that numerous modifications and variations could be made thereto by those skilled in the art without departing from the spirit and scope of the invention. In particular, the preferred embodiment describes a retinal prosthesis for artificial vision. It should be obvious to one skilled in the art that the invention has broad applicability to other types of neural stimulation. It is therefore to be understood that within the scope of the claims, the invention may be practiced otherwise than as specifically described herein.

The invention claimed is:

1. A method of determining proper placement of a neural stimulation electrode array comprising:
    placing an electrode array of an implantable neural prosthesis in proximity of neural tissue;
    sending a series of wireless command signals under automatic control to the implantable neural prosthesis to measure impedances, and thereby threshold of perception, across the electrode array after providing subthreshold of perception stimulation pulses to neural tissue on each electrode;
    communicating the impedances to a clinician via a wireless telemetry signal; determining, by the impedances, the distance between the electrode array and neural tissue, as well as any defective electrodes;
    selecting a proper chronic placement for the electrode array as the location providing the least distance between the electrode array and neural tissue, the lowest threshold of perception and the greatest dynamic range;
    attaching the electrode array chronically to neural tissue in the proper chronic placement; and
    stimulating neural percepts with the electrode array.

2. The method according to claim 1, further comprising:
    placing the electrode array in a plurality of locations;
    measuring impedance across the electrode array in each location; and
    determining, by the impedances, the best placement of the electrode array.

3. The method according to claim 1, further comprising:
    communicating the impedance to an external device; and
    displaying the impedance to a user on the external device.

4. The method according to claim 3, wherein displaying the impedance to a user is displaying the impedance to a user with a graphical representation of the plurality of electrodes.

5. The method according to claim 3, wherein displaying the impedance to a user is by sound.

6. The method according to claim 3, wherein displaying the impedance to a user is by color.

7. The method according to claim 3, wherein displaying the impedance to a user is by graphical symbol.

* * * * *